(12) United States Patent
Griffith et al.

(10) Patent No.: US 11,471,096 B2
(45) Date of Patent: Oct. 18, 2022

(54) AUTOMATIC COMPUTERIZED JOINT SEGMENTATION AND INFLAMMATION QUANTIFICATION IN MRI

(71) Applicant: THE CHINESE UNIVERSITY OF HONG KONG, Hong Kong (CN)

(72) Inventors: James Griffith, Clearwater Bay (CN); Lin Shi, Hong Kong (CN); Matthew Lun Wong, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 417 days.

(21) Appl. No.: 16/663,925

(22) Filed: Oct. 25, 2019

(65) Prior Publication Data
US 2020/0129114 A1    Apr. 30, 2020

Related U.S. Application Data

(60) Provisional application No. 62/750,732, filed on Oct. 25, 2018.

(51) Int. Cl.
*A61B 5/00* (2006.01)
*A61B 5/055* (2006.01)

(52) U.S. Cl.
CPC .............. *A61B 5/459* (2013.01); *A61B 5/055* (2013.01); *A61B 5/7267* (2013.01)

(58) Field of Classification Search
CPC ...... F16M 13/022; F16M 13/027; F16B 2/04; F16B 21/065; A47H 1/142; A47H 1/102
See application file for complete search history.

(56) References Cited

U.S. PATENT DOCUMENTS

| | | | |
|---|---|---|---|
| 9,968,257 B1 * | 5/2018 | Burt | A61B 5/0035 |
| 2008/0139920 A1 * | 6/2008 | Biglieri | G06T 7/0012 |
| | | | 600/410 |
| 2016/0035091 A1 | 2/2016 | Kubassova | |

FOREIGN PATENT DOCUMENTS

| | | | | |
|---|---|---|---|---|
| EP | 3316217 A1 * | 5/2018 | | A61B 6/03 |
| WO | WO-2018069736 A1 * | 4/2018 | | A61B 34/10 |

OTHER PUBLICATIONS

J. Folkesson, E. B. Dam, O. F. Olsen, P. C. Pettersen and C. Christiansen, "Segmenting Articular Cartilage Automatically Using a Voxel Classification Approach," in IEEE Transactions on Medical Imaging, vol. 26, No. 1, pp. 106-115, Jan. 2007, doi: 10.1109/TMI.2006.886808. (Year: 2007).*

(Continued)

*Primary Examiner* — Amelie R Davis
*Assistant Examiner* — Neshat Baset
(74) *Attorney, Agent, or Firm* — Kilpatrick Townsend & Stockton LLP

(57) ABSTRACT

Segmentation of bony regions in MRI images of joints is automated using a two-stage process. In a first stage, a machine-learning image-slice categorizer is used to categorize image slices of the MRI image data as belonging to one of a set of image-slice categories, depending on presence or absence of bone and/or tendon in the image slice. In a second stage, a first instance of a machine-learning segmentation classifier is used to segment image slices that contain both bone and tendon into bone and non-bone regions, and a second instance of a machine-learning segmentation classifier is used to segment image slices that contain bone but not tendon into bone regions and non-bone regions. Results from the two segmentation classifiers can be combined (Continued)

across image slices to provide a final segmentation of the bony structures, including inflammatory regions, in the image data.

**25 Claims, 10 Drawing Sheets
(6 of 10 Drawing Sheet(s) Filed in Color)**

(56) References Cited

OTHER PUBLICATIONS

Kayalibay, B., Jensen, G., & van der Smagt, P. (2017). CNN-based segmentation of medical imaging data. arXiv preprint arXiv: 1701.03056. (Year: 2017).*

Wang, Andrew Tsao, Martin Torriani. Boston, MA, USA. Annual Scientific Meeting Abstracts of the International Skeletal Society (ISS) 2018, Berlin, Germany. (2018). Skeletal Radiology, 47(9), 1315-1325. https://doi.org/10.1007/s00256-018-2994-5 (Year: 2018).*

Betancourt-Hernandez, M., Viera-López, G., & Serrano-Muñoz, A. (2018). Automatic Diagnosis of Rheumatoid Arthritis from Hand Radiographs using Convolutional Neural Networks. Revista Cubana de Fisica, 35(1), 39-43 (Year: 2018).*

Griffith, et al., "Computerized Quantification of Inflammatory Activity in Ankylosing Spondylitis". Paper presented in the 20th Annual Meeting & Exhibition of ISMRM, organized by International Society for Magnetic Resonance in Medicine, p. 1424. Melbourne, Australia (May 2012).

Griffith, et al., "Computer-aided assessment of spinal inflammation on MR in spondyloarthropathy," Hong Kong Journal of Radiology Award for the Best Original Paper, 5th Joint Scientific Meeting of The Royal College of Radiologists & Hong Kong College of Radiologists and 21st Annual Scientific Meeting of Hong Kong College of Radiologists, 14 pages (Nov. 2-3, 2013).

Griffith, et al., "Computer-Aided Assessment of Spinal Inflammation on Magnetic Resonance Images in Patients With Spondyloarthritis," Arthritis & Rheumatology, vol. 67, Issue 7, pp. 1789-1797 (Jul. 2015).

Ioffe, et al., "Batch Normalization: Accelerating Deep Network Training by Reducing Internal Covariate Shift," arXiv:1502.03167v3 [cs.LG], 11 pages (March 2, 2015).

Lee, et al., "Computerized Quantification of Disease Activity on MR in Patients with Spondyloarthropathy," 40th Annual Scientific Meeting, International Skeletal Society, p. 1341 (2013).

Ronneberger, et al., "U-Net: Convolutional Networks for Biomedical Image Segmentation," arXiv:1505.04597v1 [cs.CV], 8 pages (May 18, 2015).

Schilling, "The Effect of Batch Normalization on Deep Convolutional Neural Networks," KTH Royal Institute of Technology School of Computer Science and Communication, Degree Project in Computer Science and Engineering, Second Cycle, 30 credits, Stockholm, Sweden, 113 pages (2016).

Szegedy, et al., "Rethinking the Inception Architecture for Computer Vision," arXiv:1512.00567v3 [cs.CV], 10 pages (Dec. 11, 2015).

Wang, et al., "Computer-Assisted Grading of Spinal Inflammation for Patients with Spondyloarthropathy," Paper presented in The 7th International Congress on Orthopaedic Advanced Techniques and Clinical Translational Research, p. 124, Shanghai, China (May 25, 2013).

* cited by examiner

AUTOMATIC COMPUTERIZED JOINT SEGMENTATION AND INFLAMMATION QUANTIFICATION IN MRI

CROSS-REFERENCE TO RELATED APPLICATIONS

This application claims the benefit of U.S. Provisional Application No. 62/750,732, filed Oct. 25, 2018, the disclosure of which is incorporated by reference.

BACKGROUND

The present disclosure relates generally to quantification of inflammation in tissue and in particular to quantification of inflammation in joints (e.g., synovial inflammation or bone marrow edema) using magnetic resonance imaging (MRI) data and artificial neural networks.

Rheumatoid arthritis (RA) can produce inflammation in joints and tendons. The wrist and hand are is the most commonly affected body areas and are often involved in early stages of RA. Thus, there is considerable clinical interest in quantifying inflammation in the wrist (and other joints), as such quantification can be used in diagnosing RA, determining the need for treatment, monitoring progress of a treatment, and predicting outcomes. Mill allows detailed imaging of a patient's joints, allowing practitioners to visually assess inflammation.

RA typically causes two distinct types of inflammation. The first type of inflammation is inflammation in soft tissues, including inflammation of the joint lining (synovitis) and inflammation of the tendon lining (tenosynovitis), which is visible in MRI images. The second type is inflammation in the bone (osteitis), which manifests in MRI images as bone marrow edema. Osteitis is a precursor to the development of bone erosion, which can lead to largely irreversible structural damage. Increased inflammation in the bone correlates with the likelihood of erosive structural bone damage developing.

At present, inflammation observed in MRI images is assessed and broadly quantified based on visual inspection of the images. For instance, severity of osteitis is typically assessed by manually identifying each of the fifteen bone areas of the wrist (distal ends of the radius and ulna, eight carpal bones, and proximal ends of the five metacarpals) and determining, for each bone area, whether the area appears to be more or less than 50% involved with bone marrow edema. Severity of synovitis and tenosynovitis is typically assessed using a semi-quantitative grading scheme.

It would be desirable to provide techniques for quantifying joint inflammation that are more objective and more reliable than visual assessments.

SUMMARY

In order to quantify joint inflammation based on MRI images, it is generally necessary to distinguish bone regions (i.e., regions within the image that show bone tissues) from non-bone regions (e.g., regions within the image that show soft tissues such as tendons and joint linings), a process referred to herein as "segmenting" the image. At present, segmenting of images is typically done manually; automated classifiers have not been effective.

Certain embodiments of the present invention relate to methods for automating segmentation of bony regions in MRI images of joints using a two-stage process. In a first stage, an automated image-slice categorizer is used to categorize image slices of the MRI image data (e.g., coronal slices in the case of images of a wrist) as belonging to one of a set of image-slice categories, based on whether the image slice includes bony structure(s) and/or tendon. In some embodiments, the image-slice categories include: a first category of superficial image slices that do not include either bony structures or tendons; a second category of image slices that include both bony structures and tendons; and a third category of all other image slices. In a second stage, a first instance of an automated segmentation classifier is used to segment image slices of the second category into bone and non-bone regions, and a second (separate) instance of an automated segmentation classifier is used to segment image slices of the third category into bone region and non-bone regions. The output of each automated segmentation classifier is a pixel-by-pixel map indicating which pixels in the input image slice correspond to bone. A post-processing operation can be applied to the outputs of the first and second automated segmentation classifiers to generate final segmented image data. A quantification algorithm can be applied to the final segmented image data to quantify the extent of bone marrow edema.

In some embodiments, the image-slice categorizer and the segmentation classifiers can be implemented using machine-learning algorithms, such as artificial neural networks, executing on suitable computer hardware. Different machine-learning algorithms can be employed for image-slice categorization and segmentation. For instance, the image-slice categorizer can be based on the Inception v3 artificial neural network architecture while the segmentation classifiers are based on the U-Net artificial neural network architecture. The machine-learning algorithms can be trained by providing annotated image data patients exhibiting varying degrees of bone marrow edema.

The following detailed description, together with the accompanying drawings, will provide a better understanding of the nature and advantages of the claimed invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

System Overview

Figure 1:
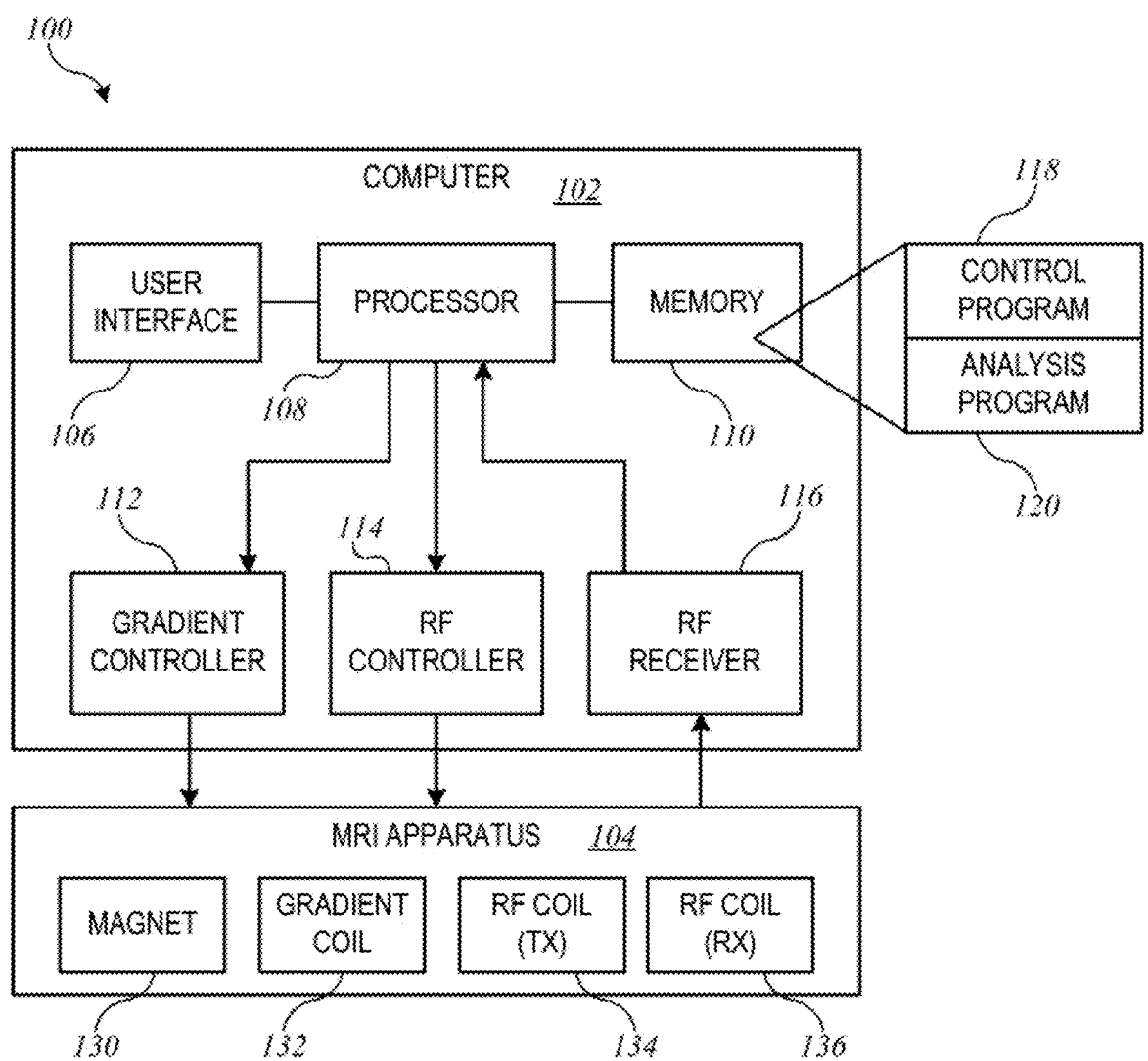
FIG. 1 shows an MRI system that can be used in connection with practicing some embodiments of the present invention.

Images of a patient's wrist (or other joint that may be affected by rheumatoid arthritis) can be obtained using MRI systems, which can be of generally conventional design. FIG. 1 shows an MRI system 100 that can be used in connection with practicing some embodiments of the present invention. MRI system 100 includes a computer 102 communicably coupled to an MRI apparatus 104.

Computer 102 can be of generally conventional design and can include a user interface 106, a processor 108, a memory 110, a gradient controller 112, an RF controller 114, and an RF receiver 116. User interface 106 can include components that allow a user (e.g., an operator of MRI system 100) to input instructions or data and to view information. For example, user interface 106 can include a keyboard, mouse, joystick, display screen, touch-sensitive display screen, and so on. Processor 108 can include one or more general purpose programmable processors capable of executing program code instructions to perform various operations. In some embodiments, processor 108 can be part of a processing system that includes one or more coprocessors such as a graphics processing unit. Memory 110 can include a combination of volatile and nonvolatile storage elements (e.g., DRAM, SRAM, flash memory, magnetic disk, optical disk, etc.). Portions of memory 110 can store program code to be executed by processor 108. Examples of the program code can include a control program 118, which can coordinate operations of MRI apparatus 104 as described below in order to acquire data, and an analysis program 120, which can perform analysis algorithms on data acquired from MRI apparatus 104. Gradient controller 112, RF controller 114, and RF receiver 116 can incorporate standard communication interfaces and protocols to communicate with components of MRI apparatus 104 as described below.

MRI apparatus 104 can be of generally conventional design and can incorporate a magnet 130, one or more gradient coils 132, and RF coils 134, 136. Magnet 130 can be a magnet capable of generating a large constant magnetic field $B_0$ (e.g., 1.5 T, 3.0 T, or the like) in a longitudinal direction, in a region where a patient can be placed. Gradient coils 132 can be capable of generating gradients along the direction of the constant magnetic field $B_0$; operation of gradient coils 132 can be controlled by computer 102 via gradient controller 112. RF coils 134, 136 can include a transmitter (TX) coil 134 and a receiver (RX) coil 136. In some embodiments, a single coil can serve as both transmitter and receiver. In some embodiments, RF transmitter coil 134 can be placed around the portion of the subject's body that is to be imaged while RF receiver coil 136 is placed elsewhere within MRI apparatus 104. The preferred placement of RF coils 134, 136 may depend on the specific portion of the body that is to be imaged; those skilled in the art with access to the present disclosure will be able to make appropriate selections.

In operation, computer 100 can drive gradient coils 132 using gradient controller 112 to shape the magnetic field around the region being imaged. Computer 100 can drive RF transmitter coil 134 using RF controller 114 to generate RF pulses at a resonant frequency for an isotope of interest, driving nuclear spins into an excited state. RF receiver coil 136 can detect RF waves (or pulses) generated by the spins relaxing from the excited state when RF pulses are not being generated. RF receiver 116 can include amplifiers, digital-to-analog converters, and other circuitry to generate digital data from the RF waves detected by RF receiver coil 136. RF receiver 116 can provide this data to processor 108 for analysis.

MRI system 100 is illustrative, and many variations and modifications are possible. Those skilled in the art will be familiar with a variety of MRI apparatus and with basic principles of MRI data acquisition, including the use of gradient fields and RF pulses, as well as techniques for detecting signals responsive to RF pulses and processing those signals to generate image data.

In accordance with some embodiments of the present invention, MRI system 100 or other MRI apparatus can be used to generate a pulse sequence suitable for T2-weighted imaging of a joint of interest, such as the wrist. The particular pulse sequence can be selected as desired, and imaging modalities other than T2-weighted MRI can be used, provided that the imaging modality produces images in which bones and soft tissues are visible and distinguishable from each other. For purposes of quantifying joint inflammation, the imaging modality should also provide a visible indication of inflammation that may be present in bone and/or soft tissue. For instance, in T2-weighted MRI, bone marrow edema appears as brighter areas within a generally dark bony structure.

Once the images are gathered, they can be analyzed to distinguish regions of bone and regions of tendon or other soft tissue, a process referred to as "segmenting" the image data. After segmenting the image data, inflammation in bone and/or tendon regions can be quantified.

Segmenting the image data for images of complex joints such as the wrist has previously been a manual operation based on visual inspection of the images. Attempts to automate segmentation of T2-weighted joint image data using convolutional neural networks have not been successful. For example, a U-Net is a structure for a convolutional deep-learning artificial neural network described in Ronneberger et al., "U-Net: Convolutional Networks for Biomedical Image Segmentation," *Miccai*, pp. 234-241 (2015) (hereinafter "Ronneberger et al."). As described in Ronneberger et al., the U-Net architecture includes a set of contracting, or downsampling, layers and a successive set of upsampling layers. The upsampling part of the U-Net architecture includes a large number of feature channels, allowing the network to propagate context information to higher-resolution layers. Automated classifiers implementing the U-Net architecture have been successfully applied to a number of image segmenting problems in the biomedical space but have not been successful in segmentation of inflammatory bony structures in T2-weighted images of joints. This is in part because areas of bone inflammation have relatively high contrast with normal (non-inflamed) bone in T2-weighted images; the contrast makes T2-weighted images useful for diagnosis but results in difficulty for the classifier in distinguishing inflammatory bone regions from soft tissue.

The inventors of the claimed invention have discovered that, in the context of segmenting images of joints, automated classifiers implementing the U-Net structure suffer from a conflicted voting problem, in which image regions having similar features result in conflicting labels, which prevents the training process from converging to a practical loss level (or from converging at all). For example, in the case of individual wrist image slices, tendons and metacarpals may be difficult for a U-Net to distinguish.

Segmentation Process

Some embodiments of the present invention provide more reliable automated segmentation techniques. As a preliminary step, individual slices of the image in the training data are categorized based on the type of tissue present. For example, in a typical MRI scan, three-dimensional data (voxels) is collected. The voxel data can be cross-sectioned in various planes to provide two-dimensional image slices. In general, a given image slice shows a cross-sectional view through the patient's body, with different slices corresponding to different cross-sections. For images of the wrist joint, coronal slices may be preferred. Different image slices of a joint may show bones, tendons, other soft tissue, and/or empty space (e.g., areas external to the patient). In some embodiments, each image slice is assigned to one of three categories: (A) superficial slices containing no bony structure; (B) slices containing both bone and tendon; and (C) all other slices. A first automated classifier can be trained to segment images in the second category (slices containing bone and tendon) into bone and non-bone regions, and a second automated classifier can be trained to segment images in the third category (which generally contain bone but little or no tendon) into bone and non-bone regions. The two automated classifiers can have identical architectures (e.g., both can be U-Nets operating on input images of the same dimensions), but they are trained independently of each other using different, non-overlapping training data sets; thus, they learn different criteria for recognizing features. Separate training of two automated classifiers resolves the conflicted voting problem and allows for significantly improved training convergence stability and accuracy in segmenting images to identify bone and soft tissue in joints.

Figure 2:
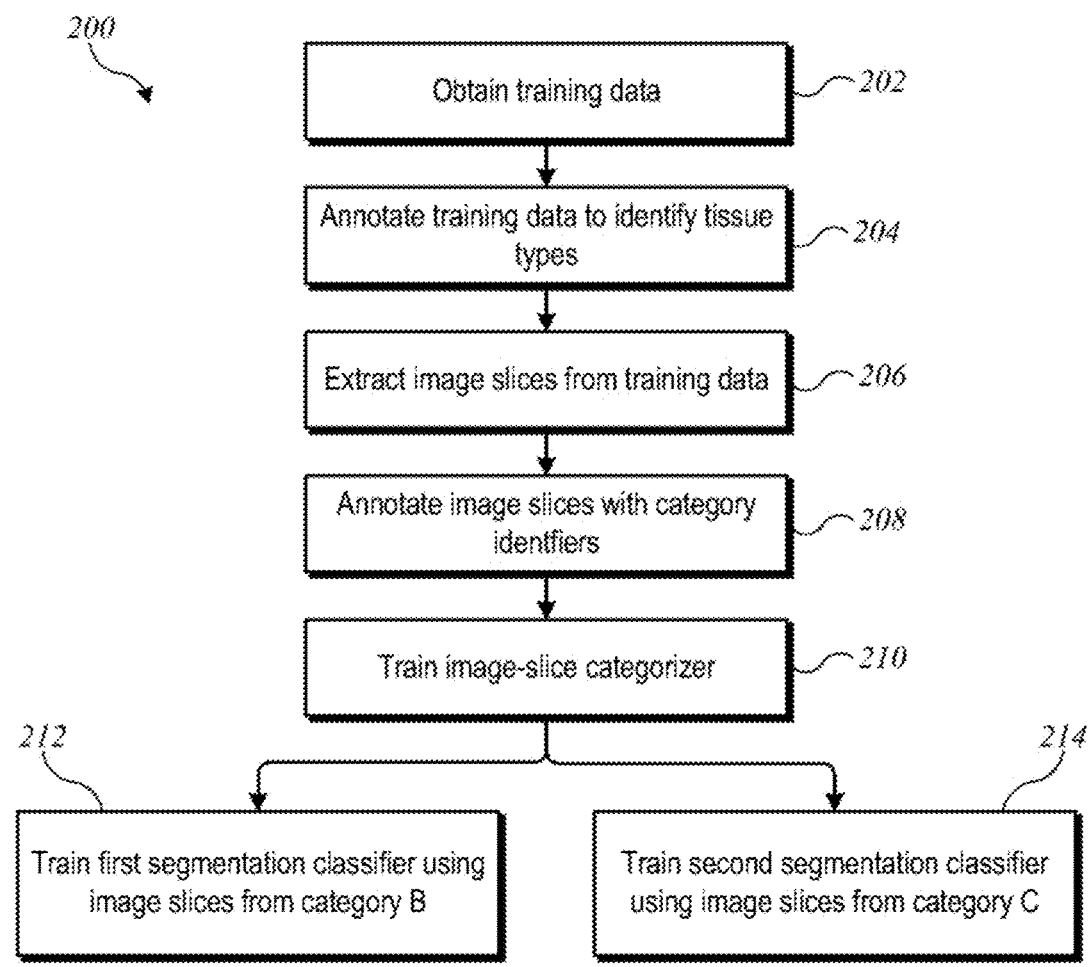
FIG. 2 is a flow diagram of a process that can be used to segment images into bone areas and soft-tissue areas according to an embodiment of the present invention.

FIG. 2 is a flow diagram of a process 200 that can be used to segment images (e.g., T2-weighted MR images) into bone areas and soft-tissue areas according to an embodiment of the present invention. Process 200 can be implemented using image data obtained from an MRI system such as system 100 of FIG. 1 and a computer system capable of executing machine-learning algorithms.

At block 202, training data for training machine-learning classifiers is obtained. The training data can include MR images of wrist joints (or other joints of interest) of a number of patients having different degrees and types of inflammation. In some embodiments, the images are T2-weighted MR images. At block 204, the training data is annotated with information identifying particular regions within the image (e.g., voxels or pixels) according to tissue type represented. In some embodiments, the identification of tissue type is a binary distinction between bone and non-bone. Annotation of training data can be done manually using conventional techniques.

Figure 3A:
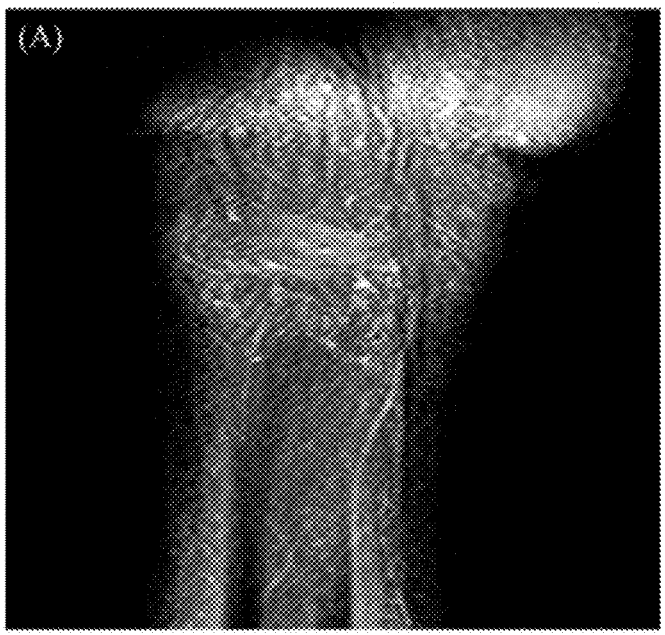
FIGS. 3A-3C show examples of image slices assigned to different image-slice categories according to an embodiment of the present invention.
Figure 3B:
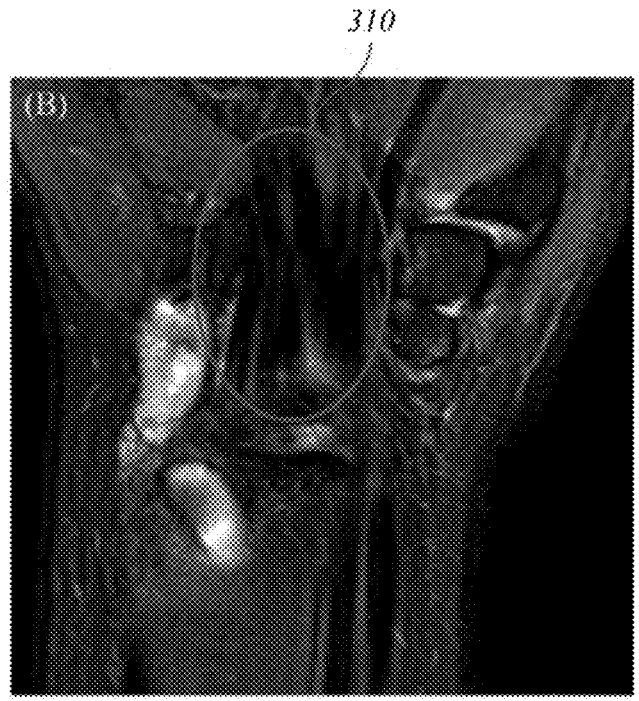
Figure 3C:
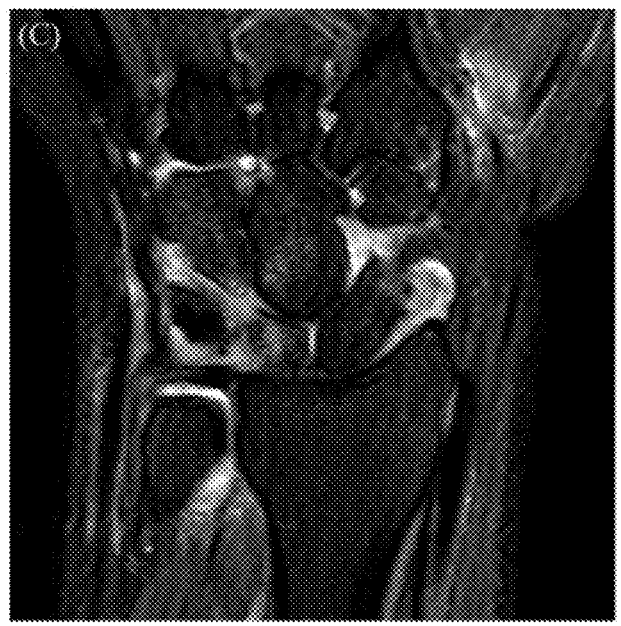

At block 206, a set of image slices can be constructed from the images in the training data. The slice direction can be chosen as desired; for instance, for wrist joints, coronal slices may be preferred. At block 208, each image slice in the training data is annotated with a category selected from a predefined set of categories. The categories can be defined based on the type(s) of tissue visible in the image slice. In some embodiments, three categories are defined. A first category (also referred to herein as "category A") is for superficial image slices that do not include any bony structures. A second category (also referred to herein as "category B") is for image slices that include both tendons and bony structures, which may be represented as dark objects in T2-weighted MR images. A third category (also referred to herein as "category C") is for all other image slices, which generally include bony structures but not tendons. By way of illustration, FIGS. 3A-3C show examples of image slices assigned to categories A, B, and C, respectively. In FIG. 3B, red outline 310 highlights a cluster of dark pixels representing tendons, which have similar features to metacarpals and may contribute to the difficulty of training a single U-Net to perform segmentation on images of wrists.

Referring again to FIG. 2, it should be noted that annotation of image slices can be done independently of the annotation of regions within an image at block 204; accordingly, blocks 204 and 206 can be performed in either order.

At block 210, an automated image-slice categorizer can be trained using the annotated image slices from block 206. The automated image-slice categorizer can be implemented using an artificial neural network or other algorithm that is capable of learning to recognize presence or absence of particular objects in an image with good accuracy and stability. One example is the Inception v3 deep convolutional network, the architecture of which is described in Szegedy et al., "Rethinking the Inception Architecture for Computer Vision," arXiv:1512.00567v3 [cs.CV] (2015). Inputs to the training process include image slices belonging to all categories and an annotation indicating the category assigned to each image slice. Annotations indicating which pixels within an image slice correspond to bone may be present but are ignored for purposes of training the image-slice categorizer. Training can proceed according to conventional machine learning techniques; an example is described below.

At block 212, a first automated segmentation classifier is trained using image slices from the second (B) category, and at block 214, a second automated segmentation classifier is trained using image slices from the third (C) category, based on the category identifiers assigned at block 208. Training of each automated segmentation classifier can happen independently of the other, and order in which the two automated segmentation classifiers are trained has no effect. If sufficient resources are available, both automated segmentation classifiers can be trained at the same time.

The first and second automated segmentation classifiers can be convolutional deep-learning neural networks or other machine-learning algorithms implemented on suitable computing hardware. The first and second automated segmentation classifiers can have the same structure (number of layers, nodes at each layer, convolution kernels, etc.); since they are trained separately, they may respond after training with different output given the same input. In some embodiments, each of the first and second automated segmentation classifiers is a U-Net, i.e., an artificial neural network having a structure as described in Ronneberger et al. The U-Net structure can be modified if desired. For instance, a batch normalization kernel can be added at the first layer and at the beginning of each downward transitional convolution layer. Batch normalization is a well-known concept in neural network architecture that can speed up training by controlling the range of outputs/inputs at a given layer, which avoids vanishing or exploding gradients in the training process. In another modification to the U-Net structure of Ronneberger et al., the upward transition merging can use plain bilinear interpolation rather than concatenation. The training input to each segmentation classifier can be image slices assigned to the relevant category, with annotations identifying bone and non-bone regions within the image (e.g., per pixel). Training can proceed according to conventional machine learning techniques; an example is described below.

Once the image-slice categorizer and the segmentation classifiers are trained, they can be used to analyze testing data. As used herein, "testing data" refers to image data that is analyzed by the trained classifiers. In the context of evaluating performance of the artificial classifiers, testing data may be annotated similarly to the training data, to facilitate comparisons between artificial neural network output and ground truth. In the context of clinical application, it is assumed that the testing data would not be manually annotated, as the goal is to rely on the artificial neural networks to perform all classification.

Figure 4:
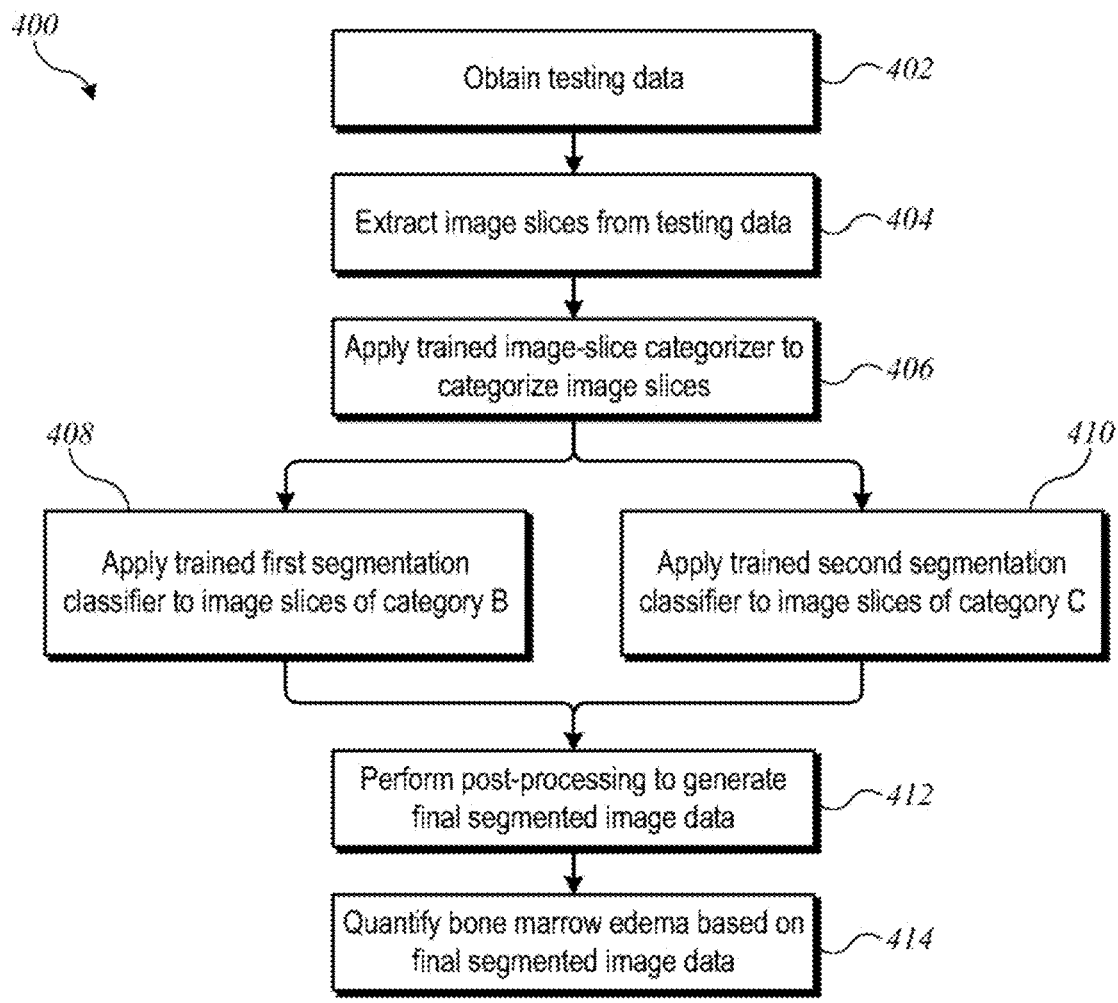
FIG. 4 is a flow diagram of an analysis process that can be used to quantify bone marrow edema in testing data according to an embodiment of the present invention.

FIG. 4 is a flow diagram of an analysis process 400 that can be used to quantify bone marrow edema in testing data according to an embodiment of the present invention. Process 400 leverages the trained automated image-slice categorizer and automated segmentation classifiers produced by process 200.

At block 402, testing data can be obtained, e.g., by performing an MRI scan on the wrist (or other joint) of a patient who is being evaluated. The testing data should be images acquired using the same modality as the training data. For instance, if T2-weighted MR images were used for training, then the testing data should also be T2-weighted MR images.

At block 404, image slices are extracted from the testing data, in a manner similar to block 206 of FIG. 2. The image slices should match the orientation (e.g., coronal) of the image slices of the training data. At block 406, the trained image-slice categorizer is applied to assign a category (e.g., category A, B, or C as defined above) to each image slice.

At block 408, the trained first segmentation classifier is applied to segment the image slices assigned to category B, and at block 410, the trained second segmentation classifier is applied to segment the image slices assigned to category C. The segmentation classifiers in this embodiment output a per-pixel classification as bone or non-bone. The two segmentation classifiers operate independently of each other and can operate separately on each image slice in their respective categories. In this embodiment, image slices assigned to category A are presumed not to contain bony structure and are not segmented.

At block 412, post-processing is performed to generate final segmented image data. In some embodiments, the post-processing can use the per-pixel classifications assigned to neighboring pixels within an image slice and/or classifications of pixels in neighboring image slices to refine the classification of each pixel as bone or non-bone. For example, post-processing can include applying sequential filters of binary hole-filling and median edge smoothing to each slice. In one example, median edge smoothing can be based on a constant radius of 3 pixels by 3 pixels by 1 pixel. Conventional filtering algorithms can be used. Post-processing can also include removing connected components (i.e., contiguous regions identified as bone) with a volume smaller than a threshold, on the theory that small components are likely to be noise rather than actual bony structures. The threshold volume can be selected to be significantly smaller than a minimum volume of a single carpal and can be, e.g., 15 mm$^3$. Other post-processing techniques may also be used.

At block 414, bone marrow edema can be quantified based on the final segmented image data. For example, conventional algorithms for quantifying bone marrow edema (BME) can be applied to the image regions (or segments) identified at block 412 as corresponding to bone. One example of an algorithm for quantifying BME is part of the RAMRIS scoring system proposed by the Outcome Measures in Rheumatology-Osteoarthritis Research Society International (OMERACT) and described in M. Østergaard et al., "OMERACT Rheumatoid Arthritis Magnetic Resonance Imaging Studies. Core Set of MRI Acquisitions, Joint Pathology Definitions, and the OMERACT RA-MRI Scoring System," *J. Rheumatology* 30(6):1385-1386 (2003) and M. Østergaard et al., "The OMERACT Rheumatoid Arthritis Magnetic Resonance Imaging (MRI) Scoring System: Updated Recommendations by the OMERACT MRI in Arthritis Working Group," *J. Rheumatology* 44(11):1706-1712 (2017). The RAMRIS scoring system includes a quantitative assessment of bone marrow edema (BME), which previously has been performed by manually segmenting and evaluating image data.

Other quantification techniques may be used in addition to or instead of RAMRIS. For example, in some embodiments synovitis can quantified based on a label obtained by subtracting bone segments identified using the process described above from a whole-tissue segmentation (i.e., all pixels representing any type of tissue).

EXAMPLE

A study to evaluate effectiveness of the techniques described herein has been conducted using data obtained from 51 participants in a cross-sectional prospective study of treatment-naïve RA patients. The patients met existing diagnostic criteria for RA with symptom duration of less than 24 months at the time of recruitment. MM imaging of the most symptomatic wrist of each patient was performed using a Philips Achieva 3.0-T scanner (available from Philips Healthcare, Best, the Netherlands). Patients were scanned in the prone position with a dedicated wrist coil to optimize signal reception. T2-weighted fat-suppressed coronal image slices were chosen for segmentation, as each bone margin can be seen most clearly on coronal images and bone marrow edema (BME) has better contrast in T2-weighted images. Each coronal image slice had a dimension of 448 pixels by 448 pixels, with a uniform pixel size of 0.178× 0.178 mm$^2$ and inter-slice spacing of 1.65 mm. The data set was randomly divided into a training set of 40 subjects (total of 818 coronal slices) and a testing set of 11 subjects (222 coronal slices). The image data for each patient was scored manually by a certified clinician using the RAMRIS scoring system.

To provide annotation for training the data, each image slice was manually classified as belonging to category A, B, or C defined above. Each image slice was also assigned an identification number to facilitate reconstructing the slices back into a volumetric image. Manual image segmentation was performed by tracing the margin of each carpal bone, the distal portion of the radius and ulna, and the proximal portions of the metacarpals on continuous image series.

The neural networks were implemented and trained using the PyTorch open-source machine learning library on a computer system with an NVIDIA TITAN Xp graphics processing unit (GPU). Optimization of network parameters (θ) used stochastic gradient descent (SGD) to minimize the negative-log-likelihood loss (L) defined as:

$$L[P(X), Y; \theta] = -\sum_{i=1}^{N} \sum_{c=1}^{C} \ln[P(x_i = c \mid y_i = c)] \quad (1)$$

where P(X) is the network output, $x_i$ is the ith component of predicted label X, $y_i$ is the ith component of ground truth Y, C is the number of classes, N is the total number of components in X or Y, each component of P(X) is a length C vector $\{P_c(x_i=c); c \in [1, C]\}$ that stores the probabilities predicted by the model with parameters θ while each component of Y contains one (ground truth) value. Learning rates $r_k$ and momentum $m_k$ were decayed before the (k+1)th according to the equations:

$$r_{k+1} = r_k \exp[-k\tau/5000] \quad (2)$$

$$m_{k+1} = \max\{0.1, m_0/2^{k/\beta}\} \quad (3)$$

where initial learning rate $r_0$, initial momentum $m_0$, learning rate decay parameter $\tau$, and momentum decay parameter $\beta$ are user-specified training parameters.

An Inception v3 artificial neural network was trained as an image-slice categorizer. Training parameters were chosen as: $r_0=1\times10^{-5}$; $m_0=0.9$; $\tau=0.005$, $\beta=1500$. A total of 10,000 training iterations, equivalent to roughly 120 training epochs, were run with a training batch size of 100.

Two instances of a U-Net classifier were separately trained to segment image slices assigned to categories B and C, respectively, identifying each pixel as either bone or non-bone. For training purposes, the manually-assigned categories were used to select images for each U-Net classifier. Training parameters for each instance were chosen as: $r_0=1\times10^{-4}$; $m_0=0.2$; $\tau=0.1$, $\beta=50$. A total of 3,000 training epochs were run with a training batch size of 6.

Testing was performed using the testing data, which was also manually annotated to allow comparisons between network output and ground truth. A process similar to process 400 was used for testing: each image slice was categorized using the trained Inception v3 categorizer, and image slices were input to the appropriate one of the two U-Net classifiers based on the output of the categorizer.

Figure 5A:
FIGS. 5A-5C show examples of image segmentation results according to an embodiment of the present invention.
Figure 5B:
Figure 5C:
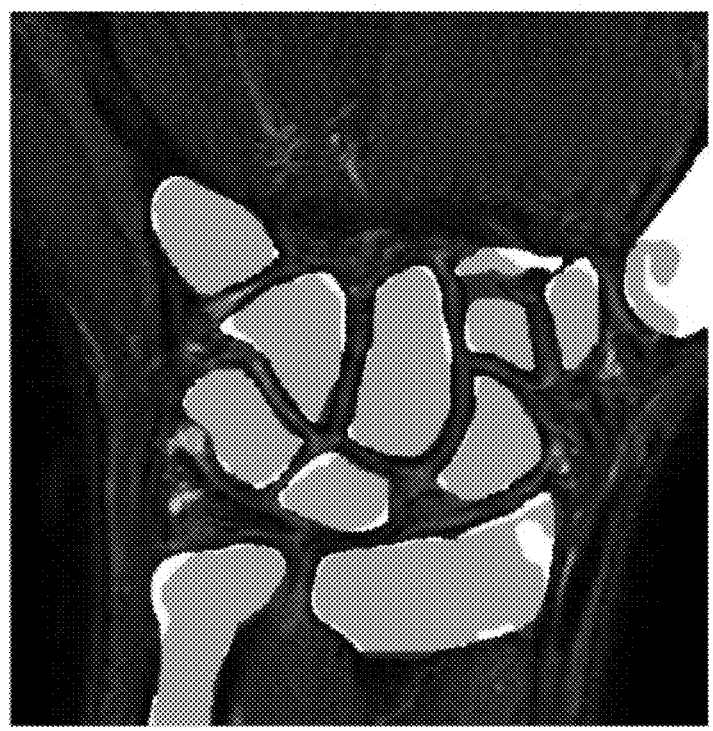

FIGS. 5A-5C show examples of image segmentation results according to an embodiment of the present invention. For each image, ground-truth (manual) segmentation is shown as an opaque white overlay, and segmentation results from the U-Net classifiers after post-processing are shown as a partially-transparent red overlay. As can be seen, the segmentation is generally accurate.

Figure 6A:
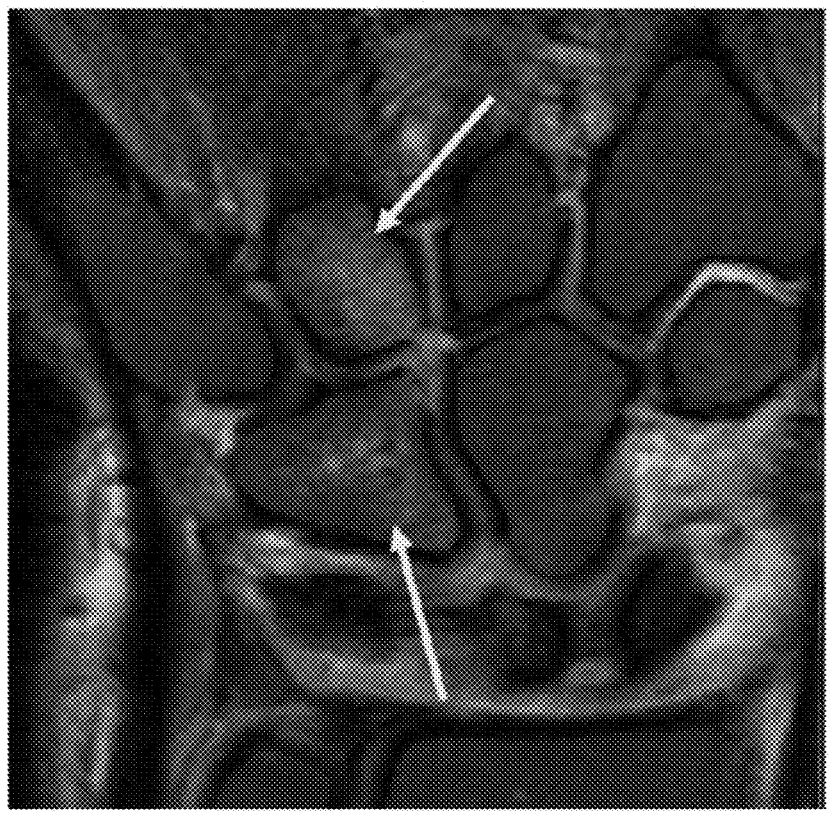
FIGS. 6A-6C show additional examples of image segmentation results according to an embodiment of the present invention.
Figure 6B:
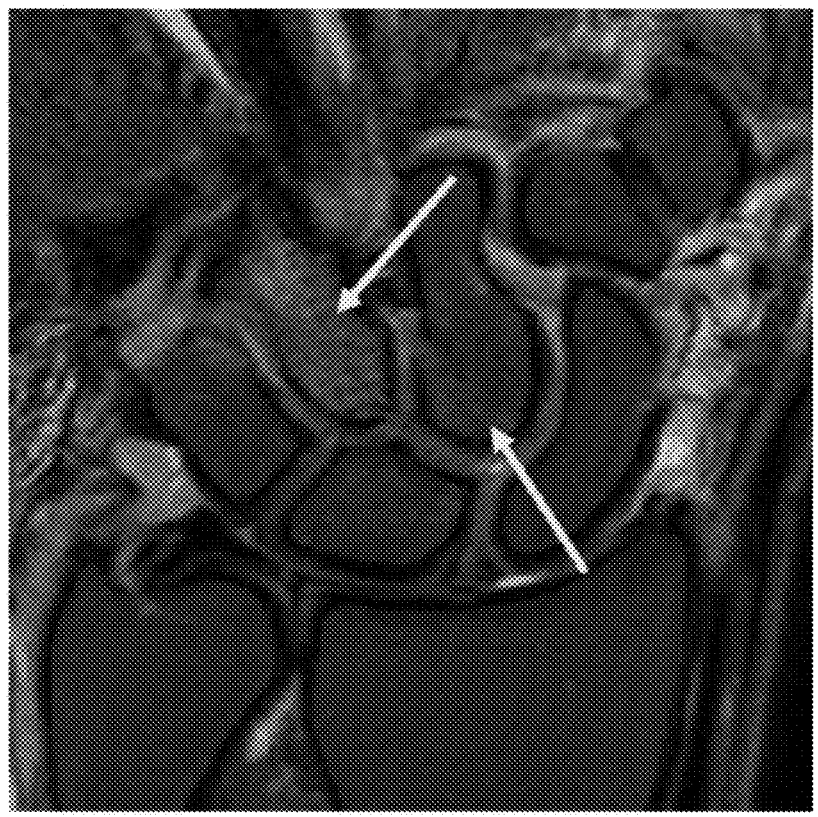
Figure 6C:
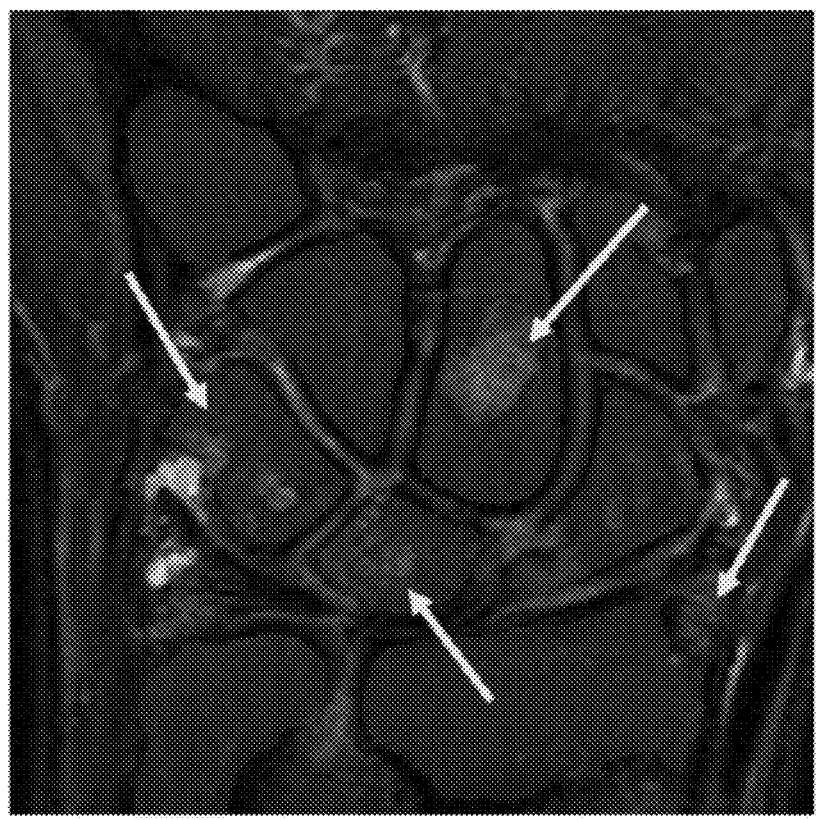

FIGS. 6A-6C show additional examples of image segmentation results according to an embodiment of the present invention. In these images, ground-truth segmentation is not shown; segmentation results from the U-Net classifiers after post-processing are shown as a partially-transparent red overlay. In these images, different degrees of bone marrow edema are present, and the yellow arrows point to edematous regions. As can be seen, the segmentation accuracy remains good even in the presence of significant bone marrow edema.

Statistical assessments of accuracy of categorization and accuracy of segmentation were also determined. Table 1 summarizes accuracy of categorization. Each row corresponds to a ground-truth (manual) category assignment and shows the number of image slices of that category that were assigned by the artificial neural network to each category (columns).

TABLE 1

| True Category | Categorizer Result | | | |
|---|---|---|---|---|
| | A | B | C | Total |
| A | 24 | 9 | 0 | 33 |
| B | 9 | 97 | 15 | 121 |
| C | 2 | 8 | 58 | 68 |
| Total | 35 | 114 | 73 | 222 |

The error rate for incorrectly assigning an image slice to category A is 4.3%, which may be improved upon given a larger training data set. It is noted that incorrectly assigning an image slice to category B or C is of less concern, since image slices in categories B or C are segmented and may contribute to evaluation of inflammation while image slices in category A are simply ignored.

For segmentation, the fitness was evaluated using DICE and Jaccard similarity coefficient (JAC) defined as follows:

$$DICE = \frac{2TP}{2TP + FP + FN} \quad (4)$$

$$JAC = \frac{DICE}{2 - DICE} \quad (5)$$

where TP is the number of true positives (pixels classified as bone in both the network output and ground truth), TN is the number of true negatives (pixels classified as non-bone in both the network output and ground truth), FP is the number of false positives (pixel classified as bone in the network output, non-bone in the ground truth), and FN is the number of false negatives (pixel classified as non-bone in the trained output, bone in the ground truth).

Error was evaluated using a global consistency error (GCE) measure, and distance of volume between network output and ground truth was defined by a volumetric distance (VD) measure normalized to between 0 and 1. More specifically:

$$GCE = \frac{1}{n}\min\left[\frac{FP(FP+2TN)}{TN+FP} + \frac{FN(FN+2TP)}{TP+FN}, \frac{FP(FP+2TP)}{TP+FP} \frac{FN(FN+2TN)}{TN+FN}\right] \quad (6)$$

$$VD = \frac{|FN - FP|}{2TP + FP + FN} \quad (7)$$

where n is the number of voxels.

Table 2 summarizes the results of the evaluation across all subjects in the testing sample. Data for the "All" category was generated using an additional instance of a U-Net that was trained on all image slices without categorization. Convergence of all tested networks was assured.

TABLE 2

| | Similarity | | Distance | |
|---|---|---|---|---|
| Category | DICE | JAC | VD | GCE |
| All | 0.840 ± 0.150 | 0.747 ± 0.179 | 0.078 ± 0.124 | 0.042 ± 0.024 |
| B | 0.862 ± 0.102 | 0.770 ± 0.138 | 0.067 ± 0.079 | 0.028 ± 0.024 |
| C | 0.939 ± 0.030 | 0.886 ± 0.050 | 0.018 ± 0.019 | 0.050 ± 0.021 |
| B + C | 0.890 ± 0.091 | 0.812 ± 0.127 | 0.049 ± 0.068 | 0.036 ± 0.025 |

As Table 2 shows, the use of a categorization stage and two separate U-Nets for categories B and C resulted in improved performance relative to a single U-Net trained to segment all image slices.

In addition, as noted above, the MRI scan for each patient was also scored using the RAMRIS standard, which includes quantifying BME. Accordingly, results could also be assessed based on RAMRIS and BME scores. It was found that the introduction of image-slice categorization prior to image segmentation, coupled with use of two segmentation classifiers, improved the accuracy of segmentation. In this example, errors in segmentation tended to be in the direction of false negatives in the carpal volume, resulting in carpal volume slightly smaller than ground truth. In the context of evaluating bone inflammation, this is believed to be acceptable error since the bone edges are not always clearly defined in MRI and since underestimating bone volume avoids inclusion of surrounding soft tissues which, if inflamed, may affect quantification of BME and/or synovitis.

Additional Embodiments

Embodiments described above provide a fully automated process for segmenting bony regions within MR images of joints. In some embodiments, segmentation result can be used to quantify or otherwise assess indicators of bone health that may be visible in the image (e.g., bone marrow edema). As described above, segmentation can be implemented in a two-stage process. In a first stage, a machine-learning image-slice categorizer is used to categorize image slices of the MRI image data as belonging to one of a set of image-slice categories, depending on presence or absence of bone and/or tendon in the image slice (e.g., in examples above, slices in category A include neither bones nor tendons; slices in category B include both bones and tendons, and all other slices are in category C). In a second stage, a first instance of a machine-learning segmentation classifier is used to segment image slices that contain both bone tissue and tendon tissue into bone and non-bone regions, and a second instance of a machine-learning segmentation classifier is used to segment image slices that contain bone tissue but not tendon tissue into bone regions and non-bone regions. Results from the two segmentation classifiers can be combined across image slices to provide a final segmentation of the image data.

While the invention has been described with respect to specific embodiments, one skilled in the art will recognize that numerous modifications are possible. All examples of images and other data are for purposes of illustration and are not intended to be limiting.

A variety of machine-learned classifiers can be used to implement image-slice categorization and image segmentation in the processes described above. For instance, the Inception v3 network used in examples above to categorize image slices may be replaced with a different machine-learning algorithm such as a support vector machine or similar classifier. Additionally or instead, additional refinement of image-slice categorization can be implemented by considering neighboring slices and imposing constraints based on human anatomy, for instance, that a category-A slice would not be expected to be present between two slices belonging to categories B and/or C.

In some embodiments, other classifier architectures may replace the U-Net architecture for image segmentation. For example, while a U-Net is able to distinguish bone regions from other regions, specifically identifying different carpals is difficult. Other classification algorithms that take fuller account of positional information (e.g., where a given pixel is in relation to the rest of the image) may be able to identify specific carpals. In other embodiments, post-processing of the U-Net output using, e.g., connected component analysis, surface point cloud k-means clustering, or the like, may also support identification of specific carpals. Parameters used for training and testing the classifiers may be varied, including the size of training data sets, size of images, number of training epochs, and so on. A particular algorithmic implementation of training is not required.

Quantification of bone inflammation can be performed on segmented image data using a number of different techniques, not limited to RAMRIS.

Further, use of the techniques described above is not limited to T2-weighted MRI image data or to MRI data. Any imaging technology that produces image slices in which bone can be distinguished from soft tissue and in which bone inflammation is observable can be used to provide data for analysis using techniques described herein. The techniques described herein are particularly useful for imaging technologies where the bone inflammation can result in automated classifiers confusing bone regions with soft tissue regions. Further, although the wrist is of clinical interest in connection with evaluating RA, the invention is not limited to this context; techniques of the kind described herein can also be applied to joints other than the wrist (e.g., ankle joints, which also include a complex arrangement of bones and tendons).

The analysis techniques described herein can be implemented using computer programs that may be executable on a variety of general-purpose or special-purpose computing devices, and those skilled in the art with access to the present disclosure will be capable of writing appropriate program code. In some embodiments, the computing device can include a central processor and one or more coprocessors, such as a graphics processing unit that can accelerate computations associated with neural network training and/or testing. The output of the computer programs may include numerical values (e.g., in list or tabular form), images (e.g., renderings generated using the image data), and/or graphical output, and may be provided on a display, on a paper printout, in an electronic document that can be transmitted via electronic communication channels (e.g., email, secure FTP server, or the like), or in any other format that can be perceived and interpreted by a clinician. It should be noted that data analysis can be but need not be performed by the MRI system used to acquire the MRI data. In some embodiments, the MRI system can be used to collect image data that is transferred to a separate computer system for analysis. Computer programs may be stored in any type of computer-readable storage medium (e.g., optical, magnetic, semiconductor-based or other non-transitory storage media) and may also be distributed using transitory computer-readable media (e.g., Internet download).

Thus, although the invention has been described with respect to specific embodiments, it will be appreciated that the invention is intended to cover all modifications and equivalents within the scope of the following claims.

What is claimed is:

1. A method for quantifying joint inflammation using magnetic resonance imaging (MRI), the method comprising:
    obtaining training data including MRI data generated by imaging a targeted joint in each a plurality of training subjects;
    training an automated categorizer to assign individual image slices of the training data to image-slice categories, wherein the image-slice category for each image slice is selected from a group consisting of:
        a first image-slice category in which the image slice is a superficial slice that does not include either bone or tendon tissue;
        a second image-slice category in which the image slice includes both bone and tendon tissue;
        a third image-slice category that includes all image slices not assigned to the first image-slice category or the second image-slice category;
    training a first automated classifier to identify bone tissue areas in an image slice, wherein training of the first automated classifier uses image slices from only the second image-slice category;
    training a second automated classifier to identify bone tissue areas in an image slice, wherein training of the second automated classifier uses image slices from only the third image-slice category;

obtaining testing data including MRI data generated by imaging the targeted joint in a test subject;

applying the trained automated categorizer and the trained first and second automated classifiers to identify bone tissue segments in the testing data, wherein applying the trained automated categorizer and the trained first and second automated classifiers includes:

applying the trained automated categorizer to assign each of a plurality of individual image slices of the testing data to one of the image-slice categories;

applying the trained first automated classifier to segment the individual image slices assigned by the trained automated categorizer to the second image-slice category;

applying the trained second automated classifier to segment the individual image slices assigned by the trained automated categorizer to the third image-slice category; and performing a post-processing operation that combines segmentation results from the trained first automated classifier and the trained second automated classifier across a plurality of image slices; and quantifying inflammation in bone tissue of the test subject, wherein quantifying inflammation in bone tissue is based on the bone tissue segments identified in the testing data.

2. The method of claim 1 wherein the targeted joint is a wrist joint.

3. The method of claim 1 wherein each of the first and second automated classifiers is a convolutional deep-learning artificial neural network.

4. The method of claim 3 wherein each of the first and second automated classifiers has a U-Net architecture.

5. The method of claim 4 wherein the U-Net architecture includes a batch normalization kernel as a first layer and at a beginning of each downward-transition convolutional layer.

6. The method of claim 5 wherein the U-Net architecture further includes a bilinear interpolation at each upward transition.

7. The method of claim 1 wherein the automated categorizer is a convolutional deep-learning artificial neural network.

8. The method of claim 7 wherein the automated categorizer has an Inception v3 architecture.

9. A computer-readable storage medium storing program instructions that, when executed by a processor of a computer system, cause the computer system to perform a method comprising:

obtaining training data including MRI data generated by imaging a targeted joint in each a plurality of training subjects;

training an automated categorizer to assign individual image slices of the training data to image-slice categories, wherein the image-slice category for each image slice is selected from a group consisting of:

a first image-slice category in which the image slice is a superficial slice that does not include either bone or tendon tissue;

a second image-slice category in which the image slice includes both bone and tendon tissue;

a third image-slice category that includes all image slices not assigned to the first image-slice category or the second image-slice category;

training a first automated classifier to identify bone tissue areas in an image slice, wherein training of the first automated classifier uses image slices from only the second image-slice category;

training a second automated classifier to identify bone tissue areas in an image slice, wherein training of the second automated classifier uses image slices from only the third image-slice category;

obtaining testing data including MRI data generated by imaging the targeted joint in a test subject;

applying the trained automated categorizer and the trained first and second automated classifiers to identify bone tissue segments in the testing data, wherein applying the trained automated categorizer and the trained first and second automated classifiers includes:

applying the trained automated categorizer to assign each of a plurality of individual image slices of the testing data to one of the image-slice categories;

applying the trained first automated classifier to segment the individual image slices assigned by the trained automated categorizer to the second image-slice category;

applying the trained second automated classifier to segment the individual image slices assigned by the trained automated categorizer to the third image-slice category; and performing a post-processing operation that combines segmentation results from the trained first automated classifier and the trained second automated classifier across a plurality of image slices; and quantifying inflammation in bone tissue of the test subject, wherein quantifying inflammation in bone tissue is based on the bone tissue segments identified in the testing data.

10. The computer-readable storage medium of claim 9 wherein the targeted joint is a wrist joint.

11. The computer-readable storage medium of claim 9 wherein each of the first and second automated classifiers is a convolutional deep-learning artificial neural network.

12. The computer-readable storage medium of claim 11 wherein each of the first and second automated classifiers has a U-Net architecture.

13. The computer-readable storage medium of claim 12 wherein the U-Net architecture includes a batch normalization kernel as a first layer and at a beginning of each downward-transition convolutional layer.

14. The computer-readable storage medium of claim 13 wherein the U-Net architecture further includes a bilinear interpolation at each upward transition.

15. The computer-readable storage medium of claim 9 wherein the automated categorizer is a convolutional deep-learning artificial neural network.

16. The computer-readable storage medium of claim 15 wherein the automated categorizer has an Inception v3 architecture.

17. A computer system comprising:

a memory storing program code; and a processing system coupled to the memory and configured by the program code to:

obtain training data including MRI data generated by imaging a targeted joint in each a plurality of training subjects;

train an automated categorizer to assign individual image slices of the training data to image-slice categories, wherein the image-slice category for each image slice is selected from a group consisting of:

a first image-slice category in which the image slice is a superficial slice that does not include either bone or tendon tissue;

a second image-slice category in which the image slice includes both bone and tendon tissue;

a third image-slice category that includes all image slices not assigned to the first image-slice category or the second image-slice category;

train a first automated classifier to identify bone tissue areas in an image slice, wherein training of the first automated classifier uses image slices from only the second image-slice category;

train a second automated classifier to identify bone tissue areas in an image slice, wherein training of the second automated classifier uses image slices from only the third image-slice category;

obtain testing data including MRI data generated by imaging the targeted joint in a test subject;

apply the trained automated categorizer and the trained first and second automated classifiers to identify bone tissue segments in the testing data, wherein applying the trained automated categorizer and the trained first and second automated classifiers includes:

applying the trained automated categorizer to assign each of a plurality of individual image slices of the testing data to one of the image-slice categories;

applying the trained first automated classifier to segment the individual image slices assigned by the trained automated categorizer to the second image-slice category;

applying the trained second automated classifier to segment the individual image slices assigned by the trained automated categorizer to the third image-slice category; and performing a post-processing operation that combines segmentation results from the trained first automated classifier and the trained second automated classifier across a plurality of image slices; and quantify inflammation in bone tissue of the test subject, wherein quantifying inflammation in bone tissue is based on the bone tissue segments identified in the testing data.

18. The computer system of claim 17 wherein the targeted joint is a wrist joint.

19. The computer system of claim 17 wherein each of the first and second automated classifiers is a convolutional deep-learning artificial neural network.

20. The computer system of claim 19 wherein each of the first and second automated classifiers has a U-Net architecture.

21. The computer system of claim 20 wherein the U-Net architecture includes a batch normalization kernel as a first layer and at a beginning of each downward-transition convolutional layer.

22. The computer system of claim 21 wherein the U-Net architecture further includes a bilinear interpolation at each upward transition.

23. The computer system of claim 17 wherein the automated categorizer is a convolutional deep-learning artificial neural network.

24. The computer system of claim 23 wherein the automated categorizer has an Inception v3 architecture.

25. The computer system of claim 17 wherein the processing system includes a central processor and a graphics processing unit.

* * * * *